United States Patent [19]

Welsh et al.

[11] Patent Number: 4,684,530

[45] Date of Patent: Aug. 4, 1987

[54] ADSORPTION OF PROTEINS FROM FLUIDS

[75] Inventors: William A. Welsh, Fulton; Yves O. Parent, Sykesville; Stanley A. Mertz, Eldersburg, all of Md.

[73] Assignee: W. R. Grace & Co., New York, N.Y.

[21] Appl. No.: 784,010

[22] Filed: Oct. 4, 1985

[51] Int. Cl.$^4$ .......................... C12H 1/04; A23L 2/30
[52] U.S. Cl. .............................. 426/330.4; 426/330.5; 426/423
[58] Field of Search ............... 426/330.3, 330.4, 330.5, 426/423, 442, 495

[56] References Cited

U.S. PATENT DOCUMENTS

| | | | |
|---|---|---|---|
| 3,617,301 | 11/1971 | Barby et al. | |
| 3,974,099 | 8/1976 | Lussier et al. | 252/453 |
| 4,027,046 | 5/1977 | Bohm et al. | 426/330.3 |
| 4,166,141 | 8/1979 | Westermann et al. | 426/422 |
| 4,479,970 | 10/1983 | Weetall | 426/253 |
| 4,490,399 | 12/1984 | Weetall | 426/330.9 |
| 4,500,554 | 2/1985 | Weetall | 426/323 |
| 4,508,742 | 4/1985 | McLaughlin et al. | 426/423 X |
| 4,515,821 | 5/1985 | Armstead et al. | 426/423 X |

FOREIGN PATENT DOCUMENTS

| | | | |
|---|---|---|---|
| 105633 | 4/1984 | European Pat. Off. | 426/423 |
| 586996 | 4/1947 | United Kingdom | 426/423 |
| 765355 | 9/1980 | U.S.S.R. | |

OTHER PUBLICATIONS

Krasd. Poly. No. SU-370830—Dated 2/7/84, Abstract.
Kokuzei-Cho No. JP-171732—dated 8/15/84, Abstract.
Corning Glass Works No. EP-118990—dated 9/19/84, Abstract.

Primary Examiner—Robert Yoncoskie
Attorney, Agent, or Firm—Jill H. Krafte

[57] ABSTRACT

Protein may be removed from fluids by adsorption onto inorganic oxide-silica cogels. Preferred cogels are silica alumina and silica magnesia activated so that the cogel surface is in acid form, with $H_0$ values less than the pH of the protein-containing fluid which, in turn, is less than the isoelectric point of the protein. The method is particularly effective for removing haze-forming proteins from wine.

19 Claims, No Drawings

ADSORPTION OF PROTEINS FROM FLUIDS

BACKGROUND OF THE INVENTION

This invention relates to a method for the adsorption of proteins from various fluids. More specifically, it has been found that proteins can be removed from fluids by adsorption onto amorphous or crystalline materials comprising acidic cogels of silica and an inorganic oxide. In particular, aluminosilicates have been found to be very effective in this adsorption process.

Examples of protein-containing fluids for which this method is effective are fruit juices, wines and protein-containing wastewater streams. Proteins are present in the juice pressed from grapes, particularly in white or rose wines which lack sufficient tannins to cause precipitation of those proteins during processing. The soluble proteins are heat labile and can be precipitated by the hot/cold cycling typically experienced during transportation and storage of wine or juice. The result is the formation of haze in the wine or juice.

The stabilization procedure presently employed by most wineries involves treatment of the wine with montmorillonite or bentonite clays. In a typical bentonite fining process, the clays are dispersed in water or wine to preswell the clay, forming a slurry. The slurry is added to the wine, where it adsorbs the proteins and various other components, and removed by settling and/or filtration. Due to small particle size and the swelling properties, the clay neither dewaters nor filters well, which presents numerous processing difficulties and results in wine loss even after additional processing of the bentonite lees. Moreover, the preparation and addition of the bentonite slurry to the wine requires significant expenditures of time, labor, energy and equipment.

Other methods, adsorptive or otherwise, have been proposed but their actual use is insignificant relative to bentonite fining. U.S. Pat. No. 4,027,046 (Bohm et al.) discloses a fining method in which a colloidal solution of silicon dioxide in water is mixed with a modifying aluminum compound and the beverage for protein removal and flocculation. Numerous other fining agents (e.g., tannin, isinglass, egg white) are employed for a variety of reasons not limited to heat stabilization. Protein removal by adsorption onto Chinese gallotannin and tannic acid on supports such as silicon dioxide has been used, as has the physical separation of proteins by ultrafiltration. Typical reasons for industry reliance on bentonite fining over these other methods are cost, effectiveness and the sensory properties of the fined wine.

SUMMARY OF THE INVENTION

By the process of this invention, proteins are removed effectively and efficiently from fluids, such as wines, by utilizing the inorganic oxide-silica cogels described herein as adsorbents for the proteins. The preferred cogels are activated to produce acidic surfaces and are sufficiently porous to permit the diffusion and adsorption of the wine protein molecules. The process is particularly effective where the $H_0$ value of the cogel surface is less than the pH of the fluid and where the fluid pH, in turn, is less than the isoelectric point of the protein to be removed.

The object of this invention is to provide a method for the adsorption of proteins from various fluids. It is a related object of this invention to provide an adsorption process in which the adsorbent resists swelling and maintains particle integrity upon contact with the protein-containing fluids. An additional object is to provide a process in which the spent adsorbent can be regenerated and recycled. Moreover, the regeneration method provided serves the additional purpose of sterilizing the adsorbent before it contacts a fresh batch of fluid.

A more specific object of this invention is to provide a rapid and efficient process for the removal of heat labile, or haze forming, proteins from wines. The use of inorganic oxide-silica cogels having surfaces with $H_0$ values of $<3.0$ maximizes adsorption efficiency while completely eliminating difficult slurry formation, sedimentation and filtration process steps necessary in bentonite fining. The cogels are easily and rapidly separated from the treated wine and there is very little wine loss connected with this new process. Of significant commercial import is the ability to use continuous process operations with this fining method and to provide for continuous on-line monitoring of the protein content. A further object is to provide a wine fining media which selectively adsorbs heat labile proteins, while leaving the original sensory characteristics of the wine relatively unaltered.

DETAILED DESCRIPTION OF THE INVENTION

It has been found that certain synthetic inorganic oxide-silica cogels have a special affinity for the adsorption of proteins from fluids under certain conditions. The process for adsorbing proteins using these cogels, as described in detail herein, essentially comprises the steps of contacting a protein-containing fluid with an activated inorganic oxide-silica cogel, where the surface $H_0$ value of the cogel is less than the pH of the protein-containing fluid, and the pH is less than the isoelectric point of the protein to be removed from the fluid, allowing proteins to be adsorbed thereon and separating the adsorbent from the protein-depleted fluid. The spent adsorbent may be regenerated and recycled. This process may be either under batch or continuous conditions, although a continuous column format better utilizes the advantages associated with the use of the cogel adsorbent of this invention.

The Adsorbent

The adsorbent used in this process is a hydrated synthetic inorganic oxide-silica cogel. This composition will be variously referred to in this specification as the "adsorbent" or "cogel."

To make the adsorbent used in this invention, a cogel is formed by preparing solutions of a silicate and the desired inorganic oxide. The silicate preferably is sodium silicate but potassium or lithium silicates could be used. The inorganic oxide most preferably is aluminum oxide, but may be magnesium, iron or titanium oxide. Silica alumina and silica magnesia adsorbents will be the most preferred for reasons of effectiveness and economy.

In the preferred embodiment, aluminosilicates (i.e., cogels of sodium silicate and aluminum oxide) are used as the adsorbent. These aluminosilicates (or silica aluminas) may be of two basic types, with either the alumina or the silicate predominating. That is, adsorbents may be used which comprise about 60.0 to 80.0% alumina or about 10.0 to 40.0% alumina.

For practical purposes, adsorbents with an excess of silica over alumina are preferred for applications of this process in which the treated fluid is potable, for example, wine or juice. Regulatory restrictions prohibit the use of an adsorbent from which aluminum can be leached into the final product. In preparing an aluminosilicate with excess silica, all the alumina can be reacted with the silica, rendering it insoluble. However, in aluminosilicates with an excess of alumina, treatment at very high temperatures, e.g., at least 800°-900° C. is necessary to insolubilize the aluminum.

The preparation of silica-alumina cogels has been discussed at length in the literature. A detailed description of a suitable process for preparing such a cogel is found in U.S. Pat. No. 3,974,099 (Lussier et al.). Briefly, sodium silicate solutions are reacted with aluminum salts (acidic, e.g., $Al_2(S_4)_3$, or basic, e.g., $NaAlO_2$) at a pH above 8.0 to form a cogel whose properties are related to the $SiO_2/Al_2O_3$ stoichiometry and processing. Alternatively, hydrosols formed by acidification of sodium silicate solutions can be mixed with aluminum salts at a pH below 4.0 to form silica-alumina cogels as a function of stoichiometry concentrations, pH, time and temperature. Adjustment of these parameters will be within the skill of the practitioner in this area. By either route, a hydrogel is made which is washed, formed and dried to yield an aluminosilicate having surface area, pore volume and pore size distribution as described below. Other cogels, such as silica magnesia, can be made by similar methods.

The cogel preferably is washed with water and then exchanged with any acid or with ammonium salts to remove exchangeable alkali metal cations. The gel preferably is activated by heating to temperatures greater than about 200.0° C., to water content of about 10.0%. This activation technique results in a cogel with a surface in acid form, that is, with low $H_0$ values. These $H_0$ values are a measure of the acidity of the solid composition and are determined as described in Catalysis: Science and Technology, Anderson et al., Ed., Vol. 2, Ch. 5, "Solid Acid and Base Catalysts" (K. Tanabe), pp. 232-272 (1981). A surface with low $H_0$ values is preferred for selective adsorption of heat labile proteins. Activation can be varied to produce surfaces with different acidity and it is generally known that higher activation temperatures will result in surfaces with lower $H_0$ values. Calcining at high temperatures (i.e., greater than 500° C.) is also desirable for improving the physical integrity of the adsorbent.

The silica adsorbent material is designed to possess porosity in pores of sufficient diameter to permit the diffusion and adsorption of the protein molecules. In the preferred embodiment of this invention, the protein-containing fluid is wine. Since the approximate diameter of typical wine proteins is about 30.0 to about 50.0 Angstroms, a cogel should be chosen for use in this embodiment which has substantial porosity contained in pores having diameters greater than about 60 Angstroms, after appropriate activation.

One convention which describes porosity is average pore diameter ("APD"), typically defined as that pore diameter at which 50% of the surface area or pore volume is contained in pores with diameters greater than the stated APD and 50% is contained in pores with diameters less than the stated APD. Thus, in cogels suitable for use in the method of this invention, at least 50% of the pore volume will be in pores of at least 60A diameter. Cogels with a higher proportion of pores with diameters greater than 60A will be preferred, as these will contain a greater number of potential adsorption sites and will offer easier accessibility to the haze-forming proteins. The practical upper APD limit is about 5000A.

The APD value (in Angstroms) can be measured by several methods or can be approximated by the following equation, which assumes model pores of cylindrical geometry:

$$APD(A) = \frac{40{,}000 \times PV \text{ (cc/gm)}}{SA \text{ (m}^2/\text{gm)}} \qquad (1)$$

where PV is pore volume (measured in cubic centimeters per gram) and SA is surface area (measured in square meters per gram).

Pore volume may be measured by the nitrogen Brunauer-Emmett-Teller ("B-E-T") method described in Brunauer et al., J. Am. Chem. Soc., Vol 60, p. 309 (1938). This method depends on the condensation of nitrogen into the pores of activated silica and is useful for measuring pores with diameters up to about 600A. If the sample contains pores with diameters greater than about 600A, the pore size distribution, at least of the larger pores, is determined by mercury porosimetry as described in Ritter et al., Ind. Eng. Chem. Anal. Ed. 17,787 (1945). This method is based on determining the pressure required to force mercury into the pores of the sample. Mercury porosimetry, which is useful from about 30 to about 10,000 A, may be used alone for measuring pore volumes in materials having pores with diameters both above and below 600A. Alternatively, nitrogen porosimetry can be used in conjunction with mercury porosimetry. For measurement of APDs below 600A, it may be desired to compare the results obtained by both methods. The measured PV is used in Equation (1).

The surface area measurement in the APD equation is measured by the nitrogen B-E-T surface area method, described in the Brunauer et al., article, supra. The surface area of all types of appropriately activated materials can be measured by this method. The measured SA is used in Equation (1) with the measured PV to calculate the APD of the material.

The adsorbent particles are similar to small, rigid sponges, with channels or pores wide enough to accept the proteins. Because of the numerous channels or pores, extensive surface area is available for protein adsorption. A typical adsorbent useful in this process may have at least about 100 square meters of surface area per gram of material, preferably at least about 200 square meters per gram.

The Substrate

It is contemplated that proteins may be removed from a variety of fluids by the method disclosed herein, provided that the conditions of fluid pH and protein isoelectric point can be met. The process is to be used to rid fluids of undesired proteins. This adsorption process is particularly useful in removing haze-forming proteins from grape juices, either fermented or unfermented. In the preferred embodiment of the invention, the protein-containing fluid is wine and the process will be described with reference to this embodiment. It is preferable to use this fining method on fermented wine. The process may be introduced at any convenient step in the overall wine-processing, prior to bottling. It also would be possible to fine the unfermented fruit juice. It should be kept in mind, however, that other fluids, such as protein-containing wastestreams, may be substituted.

The process of this invention may be used with the full range of wine varieties grown in various climates. However, the invention will find its greatest value in the processing of white or rose wines which lack sufficient tannins to cause spontaneous precipitation of proteins prior to bottling. By treating these wines according to the method of this invention, the wines may be stabilized against the formation of haze during storage and handling.

Wine proteins are a heterogenous group which do not all cause heat instability and hazing. Moreover, the protein profile and content varies among different types and varieties of wine. Typical wine proteins have molecular weight of about 8,000 to about 150,000 and average diameter of about 30.0 to 50.0 Angstroms. The typical concentration of protein in unfined wines has been assayed at about 20.0 to about 60.0 milligrams per liter.

The isoelectric point of wine proteins is about 2.8 to 4.3. A solution of proteins at the isoelectric point exhibits minimum conductivity, osmotic pressure and viscosity, and has the greatest tendency to coagulate. Typical wines have a pH of about 3.0 to about 3.5. The proteins thought to cause haze formation are believed to have a net positive charge in wine. Positively charged proteins will interact to a greater extent with the negatively charged (acidic) adsorbent surface. Thus, the conditions for this embodiment are a cogel surface $H_0$ of $<3.0$, a fluid pH of about 3.0–3.5 and protein isoelectric point of about 2.8–4.3. Under these conditions, the process effectively removes those proteins which tend to cause haze formation in the wine product.

It is desired that the fining method reduce the amount of haze-forming proteins in the wine to levels which will allow only acceptable haze formation after thermal shock. Total protein content does not directly correspond to haze formation and the object of the fining method of this invention is to reduce the haze-forming protein concentration to nearly zero. The inorganic oxide-silica cogels of this invention selectively adsorb haze-forming, or heat labile, proteins. Other chemical components, for example, those responsible for the wine's aroma, complexity and color, remain so that the wine's sensory characteristics are substantially unaltered by this treatment. In addition, the inorganic oxide-silica cogel adsorbent described herein meets all criteria for wine fining agents as described by the Bureau of Alcohol, Tobacco and Firearms, Federal Register (Sept. 24, 1984).

The heat stability (haze forming tendency) of wine typically is determined by exposing a wine sample to thermal shock, such as may be encountered during storage and handling. The wine is subjected to elevated temperatures (i.e., about 40° to 100° C.), then cooled to room temperature and chilled for a period of time at a temperature near that of ordinary refrigerated storage (i.e., about 0° to 15° C.). The haze produced after any selected heating/cooling protocol can be evaluated either visually by comparison to standards or quantitatively by turbidimetry. Following thermal cycling, haze values of less than 1.5 Nephelo turbidity units (NTUs) are generally accepted as indicating heat stability. Treatment by the stabilization method of this invention can produce wines with haze values of less than 1.0 NTU, preferably less than 0.5 NTU. Other procedures involving chemical precipitations of protein can be used in conjunction with haze evaluation, but the heating/cooling protocols are most widely used in actual practice.

The Adsorption Process

This description of the adsorption process of this invention will refer to the preferred embodiment of fining wines, as necessary. The adsorption process requires only that sufficient contact occur between the adsorbent and the wine, or other fluid, for the adsorption to occur. It will therefore be apparent that a simple batch system may be employed in which the cogel is added to a quantity of the protein-containing fluid, perhaps with agitation to increase contact, and then removed from the fluid by filtration or other convenient means. Ease of separation makes the use of this inorganic oxide-silica cogel an attractive alternative to bentonite for wine fining even in a batch process system. In this system, cogel usages typical for bentonite fining systems will be suitable. The cogels are, however, regenerable and may be re-used, in contrast to bentonite, which requires disposal.

In order to take maximum advantage of the adsorption potential of the inorganic oxide-silica cogel, a continuous, staged operation is preferred, as for example, described in Chemical Engineer's Handbook, Section 16 (5th Ed. 1973). In such a continuous flow system, the fluid to be treated (i.e., wine) flows through the solids-containing vessel, while the solid phase may be either static or in motion relative to the fluid phase and/or the containing vessel. A variety of continuous processing modes will be suitable for the process of this invention, among them an upflow or downflow fixed adsorbent bed system and an upflow expanded bed system. Single or multiple bed configurations, operating in series or in parallel, are within the scope of this process.

The ease with which the solid and liquid phases can be separated make possible a method of continuous wine fining for the first time. More efficient use of the adsorbent material is achieved through continuous processing, the overall processing time is greatly reduced as compared with bentonite fining processes, and fluid losses are virtually eliminated. The fining process of this invention easily can be integrated with other fluid handling steps in winemaking.

In an embodiment using a downflow fixed bed, one or more columns are put into place and packed with the inorganic oxide-silica cogel adsorbent in a conventional manner. The adsorbent bed may be prewetted with water or an appropriate aqueous solution, such as 0.5% aqueous citric acid or a quantity of the protein-containing fluid itself, and evacuated prior to contact with the fluid to be processed. As in conventional column adsorption, the process stream is passed through the column(s). As the fluid passes through the column(s), proteins are adsorbed onto the solid adsorbent so that a consistent outlet protein concentration is observed. In the wine fining embodiment, outlet protein concentrations are comparable to those observed for bentonite-fined wine. It is generally true that wine with the low levels of protein observed after treatment by this process will contain too few haze-forming proteins to pose problems of heat instability.

Breakthrough, represented by an increasing outlet protein concentration, indicates that the adsorbent is spent. This may be measured most conveniently with an in-line monitoring system. It is preferred that the processed fluid stream be continuously, and automatically, sampled for detection of protein. Returning again to the wine fining embodiment, a small volume of wine may be withdrawn from the process stream either intermittently or continuously. A standard haze-generating test, either chemical or physical (i.e., thermal cycling), is performed and the haze measured by a haze meter. Correlations can be made between the value of the artificially induced haze of the test procedure and the heat labile protein concentration of the processed wine. When it is determined that the adsorbent is spent, the flow may be halted or directed to another column with fresh adsorbent. Alternatively, adsorbent may be withdrawn, either continuously or intermittently, and replaced with fresh adsorbent.

Unlike bentonite which must be disposed of, the spent cogel may be regenerated and recycled. Typical inorganic oxide-silica cogel materials are stable to temperatures well in excess of 500° C. The spent material may be heated in air to temperatures sufficient to ignite adsorbed carbonaceous species, i.e., about 500° to 800° C. This treatment simultaneously regenerates the adsorption sites and sterilizes the adsorbent. The regenerated cogel then may be repacked into columns and used for fining additional quantities of protein-containing fluid.

Alternatively, an upflow, expanded bed system may be used. This is the preferred embodiment of this invention. The upflow configuration makes more effective and complete use of the adsorption sites on the cogel than the downflow packed bed. Moreover, the expanded bed configuration lends itself more readily to semi-continuous or continuous handling of the solid phase. Rates of mass transfer can be kept at a high level by using small particle sizes without the negative effect of increased pressure drop across the bed as would be encountered in a packed bed configuration. The liquid upflow rate is adjusted so that the cogel particles are fluidized or ebullient, that is, so that the particles become suspended in the flow but are not carried from the column.

Wine fined by the method of this invention is rendered resistant to haze formation without undergoing perceptible changes in the wine's chemical or sensory characteristics. Among the properties which remain essentially unaffected by contact with the inorganic oxide-silica cogel adsorbent are pH, alcohol content, total acid, total phenols, color, and sulfur dioxide, sodium, potassium and calcium content. The flavor and aroma characteristics for the inorganic oxide-silica cogel-fined wine are not affected by contact with the adsorbent (new or regenerated) and are virtually indistinguishable from raw or bentonite-fined wine. In addition, continuous flow processing may be used and substantially all of the wine may be recovered from the fining operation because of the ease in separating the wine from the fining agent. In short, this invention provides a rapid and efficient method for heat stabilizing wines.

The examples which follow are given for illustrative purposes and are not meant to limit the invention described herein. The examples are directed to various embodiments of the protein adsorption process of this invention as may be utilized in the context of removing haze-forming proteins from wines. The following abbreviations have been used throughout in describing the invention:

A—Angstrom unit(s)
APD—average pore diameter
B-E-T—Brunauer-Emmett-Teller
cc—cubic centimeter(s)
cm—centimeter
°C.—degrees Centigrade
gm—gram(s)
kg—kilogram(s)
l—liter
lb—pound(s)
m—meter
min—minutes
ml—milliliter(s)
NTU—Nephelo turbidity unit(s)
ppm—parts per million
%—percent
PV—pore volume
SA—surface area
sec—seconds
wt—weight
Wt %—weight percent

EXAMPLE 1

(Preparation of Cogel A)

A silica alumina cogel was prepared by the method described in U.S. Pat. No. 3,974,099, using the following raw materials:

4.0 Wt. % $NaAlO_2$: 19,872 gm 24 Wt. % $NaAlO_2$ was diluted with 99.0 kg $H_2O$ 4.0 Wt. % $Na_2SiO_3$: 6,624 gm 28 Wt. % sodium silicate ($SiO_2$:$Na_2O$ = 3.2) was diluted to a specific gravity of 1.040 at 33° C.

Acid/Alum: 13.2 l of 20 Wt. % $H_2SO_4$, 6.48 l of 100 gm $Al_2O_3$/l aluminum sulfate solution, 1.92 l of $H_2O$ The raw materials were pumped into an agitated tank at the following rates:

4.0 Wt. % $NaAlO_2$: 2872.0 ml/min
4.0 Wt. % $Na_2SiO_3$: 1128.0 ml/min
Acid/Alum: Sufficient to give pH = 8.0–8.5 minimum Product was collected for 36.0 minutes and dewatered on a belt filter. The filter cake was reslurried to about 10% solids and then spray dried. The collected product was washed by slurrying in water, filtering and rinsing three times with water at 70° C. The filter cake next was reslurried with an equal weight of ammonium sulfate as a 10% ammonium sulfate solution (pH 4.5–5.0) at 70° C. for five minutes and then filtered. The filter cake was reslurried to 10 Wt. % solids in a 5.0 Wt. % $(NH_4)_2CO_3$ solution at 70° C. for five minutes, then filtered and rinsed three times with water at 70° C. The product was dried in an oven at 160° C. for about 6.0 hours and was designated Cogel A. Analytical data for this product are listed in Table I.

EXAMPLE 2

(Preparation of Cogel B)

The product of Example 1 (Cogel A) was calcined for at least one hour at a temperature of about 972° C. or higher. This product was designated Cogel B. Analytical data for this product are listed in Table I.

EXAMPLE 3

(Preparation of Cogel C)

A silica alumina cogel was prepared according to the method of Example 1, except that 20 Wt. % $H_2SO_4$ was used to neutralize the mixture in place of the acid/alum. This product was identified as Cogel C. Analytical data for this product are listed in Table I.

EXAMPLE 4

(Preparation of Cogel D)

The product of Example 3 (Cogel C) was calcined for at least one hour at about 972° C. or higher. This product was designated Cogel D. Analytical data for this product are listed in Table I.

EXAMPLE 5

(Preparation of Cogel E)

A silica alumina cogel was prepared using the NaAlO$_2$ and NaSiO$_3$ solutions of Example 1. The solutions were pumped into an agitated tank at room temperature at the following rates for an SiO$_2$:Al$_2$O$_3$ ratio of 2.7:
4.0 Wt. % NaAlO$_2$: 1818.0 ml/min
4.0 Wt. % Na$_2$SiO$_3$: 2854.0 ml/min
The resulting pH of 12.8 to 13.5 was not adjusted and gelation occurred in about 30.0 seconds. Product was collected for 30.0 minutes in the tank, after which the temperature of the tank was raised to 65° C. and the slurry maintained at that temperature for one hour. The product was filtered, reslurried to about 10% solids, spray dried and then washed and dried as described in Example 1. The dried gel was calcined for one hour at 537° C. and designated Cogel E. Analytical data for this product are listed in Table I.

EXAMPLE 6

(Preparation of Cogel F)

A silica alumina cogel was prepared using the following raw materials:
12.5 Wt. % Na$_2$SiO$_3$: 157 lb. 28 Wt. % Na$_2$SiO$_3$ was diluted with 163 lb. H$_2$ to a specific gravity of 1.142 at 25° C.
Acid/Alum: 13.2 l of 20 Wt. % H$_2$SO$_4$, 6.48 l of 100 g Al$_2$O$_3$ aluminum sulfate solution, 1.92 l H$_2$O
The raw materials were pumped into an agitated tank such that the pH was between 3.6–4.0. The hydrosol was allowed to gel. The product was agitated to form a slurry and the pH was raised to 9.0 with NaOH, slurried at that pH at 85° C. for 24 hours, and spray dried. The dried product was water washed and ammonium sulfate exchanged to reduce the Na$_2$O content. The product was filtered, dried in an oven at 160° C. for 16.0 hours, calcined at 538° C. and designated Cogel F. Analytical data for this product are listed in Table I.

EXAMPLE 7

(Preparation of Cogel G)

A silica-magnesia cogel was prepared as described in Magee, J. S. et al., "Preparation and Performance of Zeolite Cracking Catalysts" in J. A. Rabo (Ed.), *Zeolite Chemistry and Catalysts*, ACS Monograph 171, American Chemical Society (1976). This was designated Cogel G. Analytical data for this product are listed in Table I.

TABLE I

| | Analytical Data for Cogel Adsorbents | | | | | | |
| | Cogels: | | | | | | |
| | A | B | C | D | E | F | G |
|---|---|---|---|---|---|---|---|
| % Na$_2$O | 0.02 | 0.02 | 0.055 | 0.055 | 0.42 | 0.27 | 0.02 |
| % SiO$_2$ | 24.1 | 24.1 | 37.6 | 37.6 | — | 92.7 | — |
| % Al$_2$O$_3$ | 75.9 | 75.9 | 63.7 | 63.7 | 25.9 | 7.03 | — |
| % MgO | — | — | — | — | — | — | 23.1 |
| Surface Area (m$^2$/gm) | 381 | 246 | 319 | 165 | 295 | 465 | 716 |
| N$_2$ Pore Volume (cc/gm) | 1.41 | 1.46 | 0.59 | 0.68 | 0.63 | 0.84 | 0.45 |
| H$_2$O Pore Volume (cc/gm) | 1.76 | — | 1.36 | — | 0.84 | — | 0.52 |
| Avg. Bulk Density (gm/cc) | 0.27 | — | 0.33 | — | 0.36 | — | 0.78 |

EXAMPLE 8

(Bentonite Fining)

For comparative analysis, bentonite fining was performed according to the following procedure. Bentonite clay grade KWK, obtained from American Colloid Co., was slowly added to deionized water at 80° C. with agitation to achieve a 5.0 Wt. % solids slurry. The slurry was permitted to stand without further heating or stirring for 72 hours. Before use, the slurry was mixed in a Waring blender.

The wines listed in Table II were fined as follows. The prepared bentonite slurry was added to each wine sample at normal usages of 0.25–1.2 gm/l, thoroughly dispersed and permitted to settle for about three days. The wine was then decanted and analyzed for protein content. Protein was measured by Bio-Rad Protein Assay (TM) (Bio-Rad Laboratories) (Coomassie Brilliant Blue G-520), using immunoglobulin G (IgG) as the protein reference standard. The results are shown in Table II.

TABLE II

| Protein Content (mg/l) of Raw and Fined Wines | | | |
| Wine Variety | Raw | Bentonite[1] | Cogel B[2] |
|---|---|---|---|
| Pinot Blanc, 1983 (CA) | 41 | 25 | 28 |
| French Colombard, 1983 (CA) | 30 | 15 | 17 |
| Chardonnay, 1983 (CA) | 47 | 12 | 14 |
| Chardonnay, 1982 (CA) | 61 | — | 12 |
| Chablis, 1982 (CA) | 37 | 19 | 15 |
| Unidentified White, 1982 (CA) | 120 | 20 | 25 |
| Elvira, 1982 (NY) | 35 | 15 | 17 |

[1] Fining procedures of Example 8.
[2] Fining procedures of Example 10.

EXAMPLE 9

(Batch Process Fining)

Batch experiments were performed to compare the effectiveness of bentonite, Cogels D, E and G, and a silica hydrogel prepared as described in U.S. Pat. No. 3,617,301. The wine used in this experiment was a California Sauvignon Blanc, 1984.

A control sample of wine which had not been exposed to any adsorbent or fining agent was analyzed for protein by the procedure described in Example 8. The fining procedure for the bentonite was as described in Example 8, using 1.2 gm bentonite per liter of wine. The fining procedure for the remaining adsorbents was as described in Example 8 except that 1.0 gm/100 ml of adsorbent was used. The resulting protein content of each sample is shown in Table III. It was demonstrated that the silica hydrogel was ineffective in reducing the protein content of the wine. The inorganic oxide-silica cogels of this invention adsorbed proteins from the wine. The adsorbents which display higher surface acidity (Cogels D and E), are superior and achieve a total protein reduction comparable to bentonite.

TABLE III

| Protein Adsorption from Wine | |
|---|---|
| Adsorbent | Protein (mg/l) |
| None | 42.0 |
| Silica Hydrogel | 35.0 |
| Cogel G | 32.0 |
| Cogel D | 6.0 |
| Cogel E | 13.0 |
| Bentonite | 10.0 |

EXAMPLE 10

(Continuous Process Fining)

Cogel B was used as the adsorbent in an experiment demonstrating a continuous process for fining several wine varieties, as listed in Table II. The process used a downflow fixed bed column, under the following operating conditions:

| | |
|---|---|
| Column Diameter | 1.5 cm |
| Bed Height | 12.0 cm |
| Bed Volume | 21.0 cc |
| Feed Rate | 16.0 cc/min |

The process stream passed through the column with a consistent outlet protein assay value, measured as in Example 8. The results are shown in Table II, in a side-by-side comparison of values for raw, bentonite fined and column fined wines. Breakthrough, represented by increasing protein content in the effluent, did occur in each case after processing a sufficient quantity of wine. This Example demonstrates that column processing with adsorbents as described herein produces wines with protein contents equivalent to those of the same wines fined with a conventional bentonite batch process.

EXAMPLE 11

(Heat Stability)

The wine evaluated in this example was a California Pinot Blanc, 1983. The bentonite fined wine (Table IV) was fined by the procedures described in Example 8. The column fined wine (Table IV) was fined in a column packed with Cogel B under the following conditions:

| | |
|---|---|
| Column Diameter | 1.5 cm |
| Bed Height | 12.0 cm |
| Bed Volume | 21.0 cc |
| Feed Rate | 16.0 cc/min |

The regenerated column fined wine (Table IV) was fined according to the same procedures as for the column fined wine, using Cogel B which was discharged from the bed, regenerated by heating to 1000° F. in air for one hour and re-packed into the column.

Raw, bentonite fined, column fined and regenerated column fined wines were subjected to the four test protocols indicated in Table IV to evaluate haze stability. Each protocol indicates a heating temperature and time period, the return to room temperature, and a chilling temperature and time period. In this experiment, a Hach Model 2100A Turbidimeter (Hach Chemical Co.) was used, with the turbidity or haze measured in Nephelo turbidity units (NTUs). The results are shown in Table V, which indicates that the column fining method of this invention produces wine of comparable heat stability to fining by conventional methods, and also demonstrates that the adsorbent of this invention may be regenerated for recycle.

TABLE IV

| Haze Stability by Various Test Protocols | | | | |
|---|---|---|---|---|
| | Turbidity Reported in Nephelo Units (NTU) | | | |
| Test Protocol | Raw Wine | Bentonite Fined | Column Fined | Regenerated Column Fined |
| 7 Mins. @ 97° C. | | | | |
| 25° C. | 15 | 0.2 | 0.5 | 0.5 |
| 24 Hrs. @ 4° C. | 19 | 0.4 | 0.6 | 0.6 |
| 6 Hrs, @ 80° C. | | | | |
| 25° C. | 16 | 0.4 | 0.4 | 0.5 |
| 24 Hrs. @ 4° C. | 22 | 1.2 | 1.0 | 1.0 |
| 16 Hrs. @ 63° C. | | | | |
| 25° C. | 12 | 0.3 | 0.3 | 0.4 |
| 24 Hrs. @ 4° C. | 15 | 0.6 | 0.7 | 0.7 |
| 48 Hrs. @ 33° C. | | | | |
| 25° C. | 3.8 | 0.3 | 0.5 | 0.4 |
| 24 Hrs. @ 4° C. | 4.5 | 0.4 | 0.5 | 0.5 |

EXAMPLE 12

(Downflow Fixed Bed Column)

Cogel D was used to process a California Sauvignon Blanc, 1984 in a downflow fixed bed column under the following conditions:

| | |
|---|---|
| Cross-Sectional Area | 5.3 cm$^2$ |
| Volume | 175.0 cc |
| Adsorbent Weight | 83.3 gm, dry basis |
| Flow Rate | 80.0 cc/min |
| Contact Time | 2.2 min |

Prior to processing the wine, two liters of a 0.5% aqueous citric acid solution were processed to wet and start up the system. The protein content of samples of the fined wine after processing of the volumes indicated in Table V was assayed by the method described in Example 8. Heat stability was measured as described in Example 11, Test Protocol #1, and also by the Bentotest (TM) (Erbsloh & Co.), in which haze was measured as described in Example 10, 20–30 seconds after adding the Bentotest (TM) solution. The results are shown in Table V, which indicates that the described adsorbent can be effectively used in a continuous process and that "breakthrough" of haze causing proteins can be detected after processing a given quantity of wine.

TABLE V

Downflow Column Processing of Sauvignon Blanc (CA, 1984) to Achieve Haze Stability

| Increment Volume Processed (cm³) | Protein Content (ppm) | Heat Stability (NTU) | Bento-test (NTU) |
|---|---|---|---|
| Starting Wine | 37.0 | 11.0 | 112.0 |
| 100 | 7.0 | 0.1 | 0.9 |
| 200 | 9.5 | 0.4 | 0.2 |
| 300 | 10.0 | 0.5 | 0.1 |
| 400 | 9.0 | 0.45 | 0.2 |
| 500 | 13.0 | 0.45 | 0.2 |
| 600 | 10.0 | 0.45 | 0.2 |
| 700 | 14.0 | 0.45 | 0.3 |
| 800 | 12.0 | 1.0 | 0.6 |
| 900 | 15.0 | 0.45 | 0.2 |
| 1000 | 18.0 | 0.5 | 1.0 |
| 1100 | 14.0 | 0.8 | 3.3 |
| 1200 | 11.0 | 0.8 | 4.3 |
| 1300 | 14.0 | 1.55 | 7.3 |
| 1400 | 15.0 | 3.0 | 7.5 |
| 1500 | 13.0 | 4.5 | 7.9 |

EXAMPLE 13

(Upflow Expanded Bed Column)

Cogel D was used to process a California Sauvignon Blanc, 1984 in an upflow expanded bed column under the following conditions:

| | |
|---|---|
| Cross Sectional Area | 19.63 cm² |
| Loaded Bed Weight | 189.63 gm, dry basis |
| Loaded Bed Volume | 392.00 cc |
| Expanded Bed Volume | 648.00 cc |
| Flow Rate | 30.50 cc/min |
| Superficial Velocity | 1.55 cm/min |
| Volumetric Flux | 1.55 cc/cm²/min |
| Expanded Bed Residence Time | 21.20 min |

The protein content of incremental volumes of the fined wine was measured by the method described in Example 8. Heat stability was measured as described in Example 11, Test Protocol #1. The results are shown in Table VI, which indicates that the described adsorbent can be effectively used in an upflow process.

TABLE VI

Fluid Bed Processing of Sauvignon Blanc (CA, 1984) to Achieve Haze Stability

| Incremental Volume Processed (cm³) | Protein Content (ppm) | Heat Stability (NTU) |
|---|---|---|
| Raw | 37.0 | 11.0 |
| 450 | 8.0 | 0.1 |
| 900 | 8.0 | 0.05 |
| 1200 | 9.0 | 0.1 |
| 1800 | 10.0 | 0.1 |
| 2700 | 8.0 | 0.1 |
| 3600 | 12.0 | 0.1 |
| 4500 | 11.0 | 0.4 |

The principles, preferred embodiments and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art without departing from the spirit of the invention.

We claim:

1. A method for removing protein from wine or fruit juice comprising:

(a) contacting said wine or fruit juice with an activated silica-alumina cogel, wherein the surface $H_o$ of said cogel is less than the pH of said wine or fruit juice, and said pH is less than the isoelectric point of the protein to be removed from the wine or fruit juice, said cogel having pores of sufficient diameter to permit the diffusion and adsorption of protein molecules, (b) allowing protein to be adsorbed onto said cogel, and (c) separating said cogel from the protein-depleted wine or fruit juice.

2. The method of claim 1 in which said cogel is activated by calcining at temperatures greater than 500° C.

3. The method of claim 2 in which said calcining temperatures are at least 800° C.

4. The method of claim 1 in which said cogel has substantial porosity contained in pores having diameters greater than about 60 Angstroms.

5. The method of claim 1 in which said cogel is prewetted with an aqueous solution prior to contacting said wine or fruit juice in step (a).

6. The method of claim 1 in which said cogel is regenerated by heating to temperatures sufficient to ignite adsorbed protein.

7. The method of claim 1 in which the surface of said silica-alumina cogel is in acid form, with an $H_o$ value of less than 3.0 in the H⁺ form.

8. The method of claim 1 in which sufficient protein is removed to render the treated wine or fruit juice resistant to haze formation when subjected to thermal shock.

9. The method of claim 8 in which the haze values of the treated wine or fruit juice are less than 1.5 NTU after being subjected to thermal shock.

10. A continuous method for removing proteins from wine or fruit juices, comprising (1) passing said wine or fruit juice through a bed of activated silica-alumina cogel, wherein the surface $H_o$ value of the cogel is less than the pH of said wine or fruit juice, and said pH is less than the isoelectric point of the protein to be adsorbed, said cogel having pores of sufficient diameter to permit the diffusion and adsorption of protein molecules, and (2) allowing protein to be adsorbed onto said cogel.

11. The method of claim 10 in which said cogel is activated by calcining at temperatures greater than 500° C.

12. The method of claim 10 in which said cogel is regenerated by heating to temperatures sufficient to ignite adsorbed protein.

13. The method of claim 10 in which said bed is a fixed bed packed with said cogel.

14. The method of claim 10 in which said bed is an upflow expanded bed with suspended particles of said cogel.

15. The method of claim 14 which further comprises continuously or intermittently withdrawing said suspended particles and continuously or intermittently adding fresh cogel.

16. The method of claim 10 in which the surface of said cogel is in acid form, with an $H_0$ value of less than 3.0 in the H⁺ form.

17. The method of claim 10 which further comprises continuously or intermittently sampling and testing the treated wine or fruit juice for haze formation.

18. The method of claim 10 in which sufficient protein is removed to render the fined wine or fruit juice resistant to haze formation when subjected to thermal shock.

19. The method of claim 18 in which the fined wine or fruit juice is characterized by haze values of less than 1.5 NTU after being subjected to thermal shock.

* * * * *